US009523112B2

(12) United States Patent
Jagesar et al.

(10) Patent No.: US 9,523,112 B2
(45) Date of Patent: Dec. 20, 2016

(54) METHOD FOR THE DETERMINATION OF THE PRESENCE OF AN ANTIBIOTIC IN A FLUID

(71) Applicant: DSM IP ASSETS B.V., Heerlen (NL)

(72) Inventors: Dhiredj Chandre Jagesar, Echt (NL); Tim De Graaf, Echt (NL); Truke Widel Smoor, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 104 days.

(21) Appl. No.: 14/348,106

(22) PCT Filed: Oct. 18, 2012

(86) PCT No.: PCT/EP2012/070643
§ 371 (c)(1),
(2) Date: Mar. 28, 2014

(87) PCT Pub. No.: WO2013/057182
PCT Pub. Date: Apr. 25, 2013

(65) Prior Publication Data
US 2015/0050679 A1  Feb. 19, 2015

(30) Foreign Application Priority Data
Oct. 18, 2011  (EP) ..................................... 11185619

(51) Int. Cl.
*C12Q 1/34* (2006.01)
*C12Q 1/18* (2006.01)
(52) U.S. Cl.
CPC .. *C12Q 1/34* (2013.01); *C12Q 1/18* (2013.01)
(58) Field of Classification Search
None
See application file for complete search history.

(56) References Cited

U.S. PATENT DOCUMENTS

2007/0148724 A1 * 6/2007 Salter .................... B01L 3/5029
435/32

FOREIGN PATENT DOCUMENTS

| EP | 0005891 A1 | 12/1979 |
| EP | 0285792 A1 | 10/1988 |
| WO | 9418343 A1 | 8/1994 |
| WO | 9623901 A1 | 8/1996 |

OTHER PUBLICATIONS

Le Breton et al. , Analytica Chimica Acta, 2007, vol. 586, p. 280-283.*
International Preliminary Report on Patentability corresponds to PCT/EP2012/070643 mailed on Jan. 29, 2014.
Gilbertson T J et al: "Modified Microbiological Method for the Screening of Antibiotics in Milk", Journal of Diary Science, American Dairy Science Association, US, vol. 78, No. 1 May 1995, pp. 1032-1038.
McEwens S A et al, "Antibiotic residues (bacterial inhibitory substances) in the milk of cows treated under label and extra-label conditions.", The Canadian Veterinary Journal. La Reveue Veterinaire Canadienne, Aug. 1992.
Sykorova Goffova, Zuzana et al., Comparison of Detection Sensitivity of Five Microbial Inhibition Tests for the Screening of Aminoglycoside Residues in Fortified Milk, Czech J. Food Sci., vol. 30, 2012, No. 4:314-320.
Neaves, Paul, "Monitoring Antibiotics in Milk—The Changing World of Test Methods", William & Neaves, The Food Microbiologists, "Moleview", 28, Randalls Road, Leaherhead, Surrey, KT22 7TQ.
Pikkemaat, Mariel G., et al., Comparison of three microbial screening methods for antibiotics using routine monitoring samples, Analytica Chimica Acta 637 (2009) pp. 298-304.
Pikkemaat, Mariel G., "Microbial screening methods for detection of antibiotic residues in slaughter animals", Anal Bioanal Chem vol. 395 (2009) pp. 893-905.

* cited by examiner

*Primary Examiner* — Kade Ariani
(74) *Attorney, Agent, or Firm* — McBee Moore Woodward & Vanik IP, LLC

(57) ABSTRACT

The present invention provides a method and test for the determination of the presence or absence of an antibiotic in a sample such as milk.

17 Claims, No Drawings

METHOD FOR THE DETERMINATION OF THE PRESENCE OF AN ANTIBIOTIC IN A FLUID

CROSS REFERENCE TO RELATED APPLICATIONS

This application is a §371 National Stage Application of PCT/EP2012/070643, filed Oct. 18, 2012, which claims priority to European Application No. 11185619.1, filed Oct. 18, 2011.

BACKGROUND

Field of the Invention

The present invention relates to a new and improved microbial growth inhibition test for the determination of the presence or absence of an antibiotic in a sample such as milk.

Description of Related Art

Nowadays, antibiotics are frequently used in veterinary practice not only for treatment of bacterial infections, but also for prophylactic purposes to improve the productivity of foodstuffs. In recent years, this irresponsible misuse of antibiotics as a preventive measure has been a decisive factor favoring the growth of bacterial resistance.

Antibiotic residues are known to be among the most frequently detected contaminants in milk and dairy products and cause important problems in this industrial sector at economical level.

To prevent the negative impact of antibiotic residues on human health and on the entire ecosystem, microbial growth inhibition tests for the determination of the presence or absence of antibiotic residues in a sample have been developed. Examples of such tests have been described in for example EP 0 005 891A and EP 0 285 792A. The tests described therein are ready-to-use tests that make use of a test organism and an indicator molecule, for instance a pH- and/or redox-indicator. The general principle of the test is that, when an antibiotic is present in a sample in a concentration sufficient to inhibit growth of the test organism, the color of the indicator will stay the same, while, when no inhibition occurs, growth of the test organism is accompanied by the formation of acid or reduced metabolites or other phenomena that will induce an indicator signal.

In general a microbial growth inhibition test will give a result within 2.5 to 4.5 hours. The long test duration is often considered as a disadvantage of microbial growth inhibition tests. Due to the long test duration, the user needs to wait for a long time for the outcome of the test and consequently further delivery or processing of the product to be tested is delayed.

In EP 0 755 456A it has been described that the duration of a microbial growth inhibition test can be reduced by using a concentration of test organism higher than $10^7$ per ml. WO 94/18343 describes that a reduction of the test duration can be achieved when a combination of two or more indicators is used. The disadvantage of both methods is that the sensitivity of the test is decreased. Furthermore, the solutions provided are too expensive.

In view of the above, there is still a need for a microbial growth inhibition test with a reduced test duration.

SUMMARY

It is an object of the present invention to provide a simple, inexpensive and easy-to-use, broadly applicable microbial growth inhibition test with a reduced test duration for the determination of the presence or absence of an antibiotic in a sample such as milk. Surprisingly, it has been found that the test duration of a microbial growth inhibition test can be reduced when a beta-lactamase is added to the test.

DETAILED DESCRIPTION OF A PREFERRED EMBODIMENT

In a first aspect the present invention is directed to a method for reducing the duration of a microbial growth inhibition test for the determination of the presence or absence of an antibiotic in a sample, the method comprising the steps of contacting a sample with a test organism, growing the test organism, detecting the amount of growth of the test organism, wherein lack of growth reflects the presence of an antibiotic in the sample, characterized in that a beta-lactamase is added to the test organism, the sample or both and the duration of the test is reduced by the addition of the beta-lactamase.

Optionally, the method comprises the step of preparing the test organism before the test organism is contacted with the sample. Therefore, the present invention is also directed to a method for reducing the duration of a microbial growth inhibition test for the determination of the presence or absence of an antibiotic in a sample, the method comprising the steps of preparing a test organism, contacting a sample with the test organism, growing the test organism, detecting the amount of growth of the test organism, wherein lack of growth reflects the presence of an antibiotic in the sample, characterized in that a beta-lactamase is added to the test organism, the sample or both and the duration of the test is reduced by the addition of the beta-lactamase.

In a further aspect the invention relates to the use of a beta-lactamase to reduce the duration of a microbial growth inhibition test for the determination of the presence or absence of an antibiotic in a sample.

In another aspect the invention is concerned with a kit comprising a beta-lactamase and a microbial growth inhibition test.

The below embodiments are applicable to all above-mentioned aspects of the invention.

In an embodiment of the invention the beta-lactamase is added before the test organism is grown, i.e. before the test is started. It can also be added after the start of the test, but this is less preferred. In an embodiment the beta-lactamase is contacted with the sample. This can be done before, during or after the sample is contacted with the test organism. In a preferred embodiment the beta-lactamase is contacted with the test organism. This can be done before, during or after the sample is contacted with the test organism. In a preferred embodiment the beta-lactamase is contacted with the test organism before the sample is contacted with the test organism. In an embodiment the beta-lactamase can be contacted with the sample and with the test organism. This can be done before test organism and sample are contacted.

The term "beta-lactamase" as used herein refers to enzymes (EC 3.5.2.6) produced by some bacteria and are responsible for their resistance to beta-lactam antibiotics like penicillins, cephamycins, cephalosporins, and carbapenems. Beta-lactamases act by breaking open the beta-lactam ring thereby deactivating the antibacterial properties of beta-lactams. Beta-lactamases can be functionally classified into four groups (groups 1 to 4). Group 2 can be divided again into six groups (groups 2a to 2f). In an embodiment the test comprises between 50 and 20,000 units/ml, preferably between 100 and 15,000 units/ml, more preferably between 250 and 10,000 units/ml and in particular between 300 and 8,000 units/ml beta-lactamase. Unit as used herein is defined as follows: one unit hydrolyzes 1.0 micromole of benzylpenicillin per minute at pH 7.0 at 25° C.

In an embodiment the microbial growth inhibition test comprises an indicator. The term "indicator" refers to a substance used to measure (for example by change of colour or fluorescence) the condition of a test medium with respect to the presence of a particular component (for example an acid, a base, oxidizing or reducing agents). Particularly useful are indicators that, upon changing from one state to the other, provide a visually detectable signal such as a change in color or fluorescence. The amount of indicator in the test medium is generally between 0.01 and 50 g/l test medium, preferably between 0.1 and 10 g/l, more preferably between 0.5 and 5 g/l, most preferably between 1 and 3 g/l. The indicator may be a pH-indicator, a redox-indicator or a combination thereof. The term also may refer to two or more indicators. The skilled artisan will appreciate that many indicators are suitable for the purpose of the present invention. Examples of suitable indicators can be found in handbook H. J. Conn's Biological Stains, R. D. Lillie ed., Baltimore, 1969.

The test may have the form of a liquid, a solid or a gel-like matrix. In an embodiment of the invention the microbial growth inhibition test further comprises a gelling agent. The term "gelling agent" as used herein refers to a compound that assists in changing a mixture into a gel or taking on the form of a gel. Examples of suitable gelling agents in the various aspects of the present invention include, but are not limited to, agar, gelatin, alginic acid and salts thereof, carrageenan, locust bean gum (Carob gum), hydroxypropyl guar and derivatives thereof, processed eucheuma seaweed and the like. Agar is the preferred gelling agent. In an embodiment a test organism and an indicator and optionally other additional ingredients such as the beta-lactamase are introduced into an agar solution. The agar solution is allowed to solidify to form the test medium such that the test organism stays alive, but cannot multiply because of e.g. low temperature. The amount of gelling agent in the test is generally between 1 and 200 g/l test medium, preferably between 2 and 50 g/l, more preferably between 5 and 20 g/l, most preferably between 7 and 15 g/l.

When the test medium has the form of a solid matrix, it may comprise a carrier material such as a ceramic, cotton, glass, a metal particle, a polymer in any shape or form, a silicate, a sponge, wool and the like. Alternatively, the test may have the form of a tablet, disc or paper filter comprising the test organism, indicator and optionally nutrient. The three constituents may be present in a single tablet, but also in two or more tablets. Of course, test systems combining test media in solid, liquid and/or gel-like form may be used.

Optionally, the microbial growth inhibition test may also contain nutrients, stabilizers, salts, buffers and/or viscosity-increasing agents. The term "nutrient" as used herein refers to a nutritive substance or ingredient that promotes and/or is required for the growth of the test organism. Suitable nutrients depend from the microorganism used in the test system. The test medium may comprise two or more different nutrients. They include, but are not limited to, assimilable carbon sources such as carbohydrates such as e.g. glucose, fructose, sucrose, lactose and dextrose; assimilable nitrogen sources such as amino acids such as e.g. peptone or tryptone; sources of vitamins and growth factors such as beef or yeast extract; and sources of minerals such as earth alkaline metal salts such as salts of e.g. barium or calcium. Suitable additional ingredients that may be present in the test according to the present invention are known to the person skilled in the art and include, but are not limited to, agents that increase or decrease the sensitivity of the test for antibiotics.

In an embodiment of the invention the test organism is selected from the group consisting of a *Bacillus* species, an *Escherichia* species and a *Streptococcus* species. In a preferred embodiment of the invention the test organism is thermophilic. Examples are *Bacillus stearothermophilus* or *Streptococcus thermophilus*, with *Bacillus stearothermophilus* being preferred. These species may be introduced in the test as units capable of producing colonies, or Colony Forming Units (CFUs). The term "CFU" as used herein refers to the number of test organisms, spores of test organisms, partially germinated spores of test organisms, vegetative cells or any mixture thereof capable of producing colonies of organisms. The concentration of said CFUs is expressed as Colony Forming Units per ml of test medium (CFU/ml) and is usually in the range of $1\times10^5$ to $1\times10^{12}$ CFU/ml, preferably $1\times10^6$ to $1\times10^{10}$ CFU/ml, more preferably $2\times10^6$ to $1\times10^9$ CFU/ml, most preferably $5\times10^6$ to $1\times10^8$ CFU/ml, or still more preferably $5\times10^6$ to $2\times10^7$ CFU/ml.

In an embodiment of the invention the sample may be derived from a body liquid, an organ, meat or eggs. Antibiotics might also be present in food products in which these animal products are added as an ingredient. Examples of food products are milk; meat of cow, pig, poultry and fish; sea food such as shrimps; liver; processed meat products such as sausages; ready-to-eat meals and baby food. Antibiotics might also be present in body liquids or animal tissues, which are suitable for examination by for example food inspection authorities. Examples are blood, kidney tissue or pre-urine obtained from the kidney and urine. Urine and blood are suitable for examination prior to slaughtering of the animal. Antibiotics may also be present in waste water, water from any type industry, etc. In a preferred embodiment the sample is urine, blood, egg, honey, kidney, meat, liver, fish, shrimp, feed and/or milk, with milk being most preferred. In a preferred embodiment the sample is a fluid sample. In an embodiment the sample might not be fluid and fluid comprising the antibiotic(s) needs to be extracted from the sample.

In an embodiment of the invention the test is able to determine the presence or absence of an antibiotic in a sample. The antibiotic to be determined can be an antibiotic from a family of antibiotics that is selected from the group consisting of the family of beta-lactam antibiotics, the family of tetracycline antibiotics, the family of sulfonamide antibiotics, the family of aminoglycoside antibiotics, and the family of quinolone antibiotics. In a preferred embodiment of the invention the antibiotic to be determined is an antibiotic from a family of antibiotics that is selected from the group consisting of the family of beta-lactam antibiotics, the family of tetracycline antibiotics and the family of sulfonamide antibiotics. Examples of beta-lactam antibiotics are penicillin derivatives (penams), cephalosporins (cephems), monobactams, penems and carbapenems. Examples of penams, cephems, monobactams, penems and carbapenems are known to the skilled artisan.

Preferably, there is minimal or no germination and outgrowth of the test organism prior to the addition of fluid sample. This is achieved by storing and keeping the test under conditions comprising an unfavorable temperature and/or an unfavorable pH-value and/or the absence of nutrients essential for germination and outgrowth of the test organism. Of course, the conditions should not cause irreversible damage to all CFUs present in the microbial growth inhibition test.

After contacting the sample with the test organism, growth of the test organism is allowed to take place during a period sufficiently long for the test organisms to grow in case no antibiotic is present. Growth is induced by adding nutrients, optionally before the contacting of said sample, and/or raising the temperature, and/or providing for a pH-value at which the test organism is able to grow. Alternatively, these conditions may be established prior to contact of the fluid sample with the test organism.

The amount of growth of the test organism is detected by observing the presence or absence of a change of the indicator. Lack of growth reflects the presence of an antibiotic in the sample. As indicated above, the presence or absence of an antibiotic is determined by the presence or absence of a change of the indicator(s) used. When, for example such a change is a color change, said color change may be observed visually. However, said color change may also be determined using an arrangement that generates digital image data or an arrangement that generates analog image data and converts said analog image data into digital image data followed by interpretation of said digital image data by a computer processor. An example of such an arrangement, i.e. a sample-reading device such as a scanner coupled to a personal computer, is described in WO 03/033728. Another example of such an arrangement, i.e. a combined sample incubating and sample-reading device (such as a scanner combined with an incubator) coupled to a personal computer is described in WO 2007/090683. Both documents are herewith incorporated by reference.

Optionally, certain test ingredients are sterilized and usually the pH of the test is adjusted to the required value. Optionally, samples may be mixed (e.g. with other samples, but also with salts, buffering compounds, nutrients, stabilizers, enzymes, and the like), concentrated and/or diluted (e.g. with diluting liquids such as water, solvents, and the like) prior to addition to the test organism.

In an embodiment of the invention, the test organism is grown by incubating it for a predetermined period, preferably within a time span of 0.5 to 6 hours, more preferably between 0.75 to 5 hours, most preferably between 1.0 to 4 hours. Preferably the test organism is incubated at a predetermined temperature, preferably the optimal growth temperature of the test organism. When, for example, thermophilic test organisms are used, said temperature is preferably between 40 and 70° C., more preferably between 50 and 65° C., most preferably between 60 and 64° C. Optionally said reaction can be carried out with the aid of a thermostatic device. Alternatively, the time required for growth of the test organism is equal to the time that is required for a calibration sample with a known amount of antibiotic to induce a change in the indicator.

In an embodiment of the invention the test organism is present in one or more containers. Optionally, the containers are part of a kit which further comprises a beta-lactamase. The beta-lactamase may also be present in one or more containers. The kit may further comprise a sampling device. The containers may be test tubes of any shape and size and from any material available, provided that observation of indicator changes is possible. Also, the containers may be wells such as those incorporated in microtiter plates. A sampling device is a device with the aid of which fluid can be added to the microbial growth inhibition test. Examples include, but are not limited to, a container (optionally with volume markings) a syringe, a pipette or an automated pipetting system. Such a syringe or pipette may be designed in such a fashion that with only one mode of operation a predetermined volume can be withdrawn from the fluid sample to be analyzed. Optionally, systems known in the art with which more than one syringe or pipette can be operated with one single handling may be applied. Optionally, the kit further comprises means for sealing of said containers filled with test organism during incubation and/or an insert with instructions for use and/or a means for setting the time needed for incubation.

Optionally, the ratio of the sample to test medium exceeds 2:3 (0.68:1) (v/v). Preferably, said ratio is at least 20:27 (0.74:1) (v/v), more preferably said ratio is at least 25:27 (0.93:1) (v/v); most preferably said ratio is at least 2:1 (v/v). It has been found that there is no technical reason for an upper limit to the amount of sample. In practice, this volume should not exceed the maximum content of the container that holds the test medium. For example, in a 2 ml container having 0.2 ml test medium, no more than 1.8 ml of fluid sample should be added. In practice, containers for performing the method of the present invention have a volume that rarely exceeds 50 ml and hence the amount of fluid sample to be added shall not exceed 50 ml, preferably 10 ml, more preferably 5 ml, still more preferably 2 ml, most preferably 1 ml. Thus, in general, the upper limit of the ratio of the volume of fluid sample to the volume of test medium is 250:1 (v/v), preferably 50:1 (v/v), more preferably 25:1 (v/v), still more preferably 10:1 (v/v), most preferably 5:1 (v/v). In a preferred embodiment the volume of the dilution/sample is greater than the volume of test medium.

Optionally, the kit further comprises a thermostatic device, with the aid of which samples can be kept at a pre-set temperature, such as the temperature at which the test organism shows sufficient growth. Preferably, said thermostatic device is designed in such a fashion that it can hold said containers filled with the test organism. Optionally, the thermostatic device is coupled to a means for setting the time needed for incubation such that heating and/or cooling is stopped after lapse of a pre-set period.

Optionally, the kit further comprises a data carrier loaded with a computer program suitable for instructing a computer to analyze digital data obtained from a sample-reading device. Said data carrier may be any carrier suitable for storing digital information such as a CD-ROM, a diskette, a DVD, a memory stick, a magnetic tape or the like. Advantageously, said data carrier loaded with a computer program provides for easy access to the latest available computer programs suitable for use in the method of the present invention.

EXAMPLES

Example 1

Effect of Beta-Lactamase on the Test Duration of Delvotest® SP-NT DA Test

In order to establish the effect of beta-lactamase on the test duration of the Delvotest® SP-NT DA test, the following series of experiments was carried out. As a control, a commercially available Delvotest® SP-NT DA test without any added beta-lactamase (DSM Delvotest® SP-NT DA plates containing 8×12 test wells per plate) was used. More information on the Delvotest® SP-NT DA test can be found in Journal of AOAC International, volume 95, pages 252-260. In addition, three different tests were prepared by modifying control test plates by adding beta-lactamase (in different concentrations, see Table 1) to test medium, mixing the obtained medium and filling in the individual wells of the plates with the mixed test medium. Consequently, the following plates were obtained:
- a plate with test wells comprising no beta-lactamase (control test),
- a plate with test wells comprising 2000 units/ml beta-lactamase per well,
- a plate with test wells comprising 4000 units/ml beta-lactamase per well, and
- a plate with test wells comprising 6000 units/ml beta-lactamase per well, The difference in time required for a sample without antibiotic to induce a change in indicator (and thus in color) of the tests with beta-lactamase compared to the control test was determined.

Milk (100 µL) was added to the test medium (170 µL) in each well and incubated at 63° C. in a Delvotest Reader/Incubator device (see WO 2007/090683). The color of the test wells containing the milk samples was continuously monitored by the device. The color of each test well is expressed as a Z-value; a purple color (no growth of test organism) gives rise to a positive Z-value, while a yellow color (growth of test organism) has a negative Z-value. For Delvotest SP-NT DA, the control time is the point in time where the Z-value of at least 10% of the milk samples is below a Z-value of −12. The control time is the duration of the test. Detailed descriptions of the scanning technology and the expression of the color in Z-values can be found in WO 2007/090683.

TABLE 1

Test duration of a test system without beta-lactamase (i.e. a control system) and test systems with beta-lactamase.

| Amount of beta-lactamase (in Units/ml) added to control test (DSM Delvotest ® SP-NT DA) | T (min) | ΔT (min) |
|---|---|---|
| — | 125 | — |
| 2000 | 122 | −3 |
| 4000 | 121 | −4 |
| 6000 | 115 | −10 |

T = test duration
ΔT = difference in test duration compared to control test

The results indicate that addition of beta-lactamase to the test results in a test having a significantly shorter test duration compared to the control test.

Example 2

Effect of Beta-Lactamase on the Test Duration of Delvotest® T Test

In order to establish the effect of beta-lactamase on the test duration of the Delvotest® T test, the following series of experiments was carried out. As a control, a commercially available test without any added beta-lactamase (DSM Delvotest® T plates containing 8×12 test wells per plate) was used. Delvotest® T test is a standard diffusion test for the detection of residues of antibacterial substances (antibiotics). The test comprises a solid agar medium seeded with a number of spores of *Bacillus stearothermophilus* together with required nutrients for growth purposes. The test further comprises a pH indicator. Samples which are free from antibacterial substances or contain them below specified levels will, when added to the test, allow germination and growth of the bacteria. This will lead to change in color of the indicator. When samples contain antibacterial substances at or above the test sensitivity, growth is inhibited and as a result the color remains the same.

In addition, three different tests were prepared by modifying control test plates by adding beta-lactamase (in different concentrations, see Table 2) to test medium, mixing the obtained medium and filling in the individual wells of the plates with the mixed test medium. Consequently, the following plates were obtained:
- a plate with test wells comprising no beta-lactamase (control test),
- a plate with test wells comprising 2000 units/ml beta-lactamase per well,
- a plate with test wells comprising 4000 units/ml beta-lactamase per well, and
- a plate with test wells comprising 6000 units/ml beta-lactamase per well, The difference in time required for a sample without antibiotic to induce a significant change in indicator (and thus in color) of the tests with beta-lactamase compared to the control test was determined.

Milk (100 µL) was added to the test medium (170 µl) in each well and incubated at 64° C. in a water bath. The point in time where all wells of a plate changed color from purple to yellow was visually determined. This point in time is the control time and considered the test duration.

TABLE 2

Test duration of a test system without beta-lactamase (i.e. a control system) and test systems with beta-lactamase.

| Amount of beta-lactamase (in Units/ml) added to control test (DSM Delvotest ® T) | T (min) | ΔT (min) |
|---|---|---|
| — | 195 | — |
| 2000 | 185 | −10 |
| 4000 | 175 | −20 |
| 6000 | 172 | −23 |

T = test duration
ΔT = difference in test duration compared to control test

The results indicate that addition of beta-lactamase results in a test having a significantly shorter test duration compared with the control test.

The invention claimed is:

1. A method for reducing the duration of a microbial growth inhibition test, that comprises an indicator, for determining the presence or absence of a beta-lactam antibiotic, a tetracycline antibiotic, a sulfonamide antibiotic, an aminoglycoside antibiotic or a quinolone antibiotic in a sample, the method comprising:
   (a) contacting a sample with a test organism,
   (b) growing the test organism in the presence of the indicator by adding nutrients, and/or raising the temperature, and/or providing for a pH-value at which the test organism is able to grow,
   (c) detecting an amount of growth of the test organism by observing the presence or absence of a change of the indicator, wherein lack of growth of the test organism is determined by absence of a change of the indicator, and wherein lack of growth reflects a presence of a beta-lactam antibiotic, a tetracycline antibiotic, a sulfonamide antibiotic, an aminoglycoside antibiotic and/ or a quinolone antibiotic in the sample,
   wherein between 50 and 20,000 units/ml of a beta-lactamase is added to the test organism before the test is started, and/or added to the sample before, during or after the sample is contacted with the test organism and wherein the beta-lactamase reduces the duration of the microbial growth inhibition test compared to the duration of the microbial growth inhibition test performed without beta-lactamase.

2. The method according to claim 1, wherein the beta-lactamase is added before the test organism is grown.

3. The method according to claim 1, wherein the indicator is a pH indicator and/or a redox indicator.

4. The method according to claim 1, wherein the test organism is selected from the group consisting of a *Bacillus* species, an *Escherichia* species and a *Streptococcus* species.

5. The method according claim 1, wherein the sample is a fluid sample.

6. The method according to claim 5, wherein the sample is milk.

7. The method according to claim 1, wherein the test organism is thermophilic.

8. The method according to claim 1, wherein the microbial growth inhibition test further comprises a gelling agent.

9. The method according to claim 7, wherein the test organism is selected from the group consisting of *Bacillus stearothermophilus* or *Streptococcus thermophilus*.

10. The method according to claim 1, wherein the microbial growth inhibition test is for determining the presence or absence of a beta-lactam antibiotic in a sample.

11. The method according to claim 1, wherein the microbial growth inhibition test is for determining the presence or absence of a tetracycline antibiotic in a sample.

12. The method according to claim 1, wherein the microbial growth inhibition test is for determining the presence or absence of a sulfonamide antibiotic in a sample.

13. The method according to claim 1, wherein the microbial growth inhibition test is for determining the presence or absence of an aminoglycoside antibiotic in a sample.

14. The method according to claim 1, wherein between 100 and 15,000 units/ml of a beta-lactamase is added to the test organism before the test is started, and/or added to the sample before, during or after the sample is contacted with the test organism.

15. The method according to claim 1, wherein between 250 and 10,000 units/ml of a beta-lactamase is added to the test organism before the test is started, and/or added to the sample before, during or after the sample is contacted with the test organism.

16. The method according to claim 1, wherein between 300 and 8,000 units/ml of a beta-lactamase is added to the test organism before the test is started, and/or added to the sample before, during or after the sample is contacted with the test organism.

17. The method according to claim 1, wherein between 2,000 and 6,000 units/ml of a beta-lactamase is added to the test organism before the test is started, and/or added to the sample before, during or after the sample is contacted with the test organism.

* * * * *